United States Patent
Chen

(10) Patent No.: US 11,673,849 B2
(45) Date of Patent: *Jun. 13, 2023

(54) PROCESS FOR SELECTIVATING CATALYST FOR PRODUCING PARAXYLENE BY METHYLATION OF BENZENE AND/OR TOLUENE

(71) Applicant: ExxonMobil Chemical Patents Inc., Baytown, TX (US)

(72) Inventor: Tan-Jen Chen, Seattle, WA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/271,451

(22) Filed: Feb. 8, 2019

(65) Prior Publication Data

US 2019/0330129 A1    Oct. 31, 2019

Related U.S. Application Data

(63) Continuation of application No. 15/702,469, filed on Sep. 12, 2017, now Pat. No. 10,246,387.

(60) Provisional application No. 62/437,493, filed on Dec. 21, 2016.

(51) Int. Cl.
| | |
|---|---|
| *C07C 15/08* | (2006.01) |
| *B01J 29/70* | (2006.01) |
| *C07C 15/06* | (2006.01) |
| *C07C 15/04* | (2006.01) |
| *B01J 29/03* | (2006.01) |
| *C07C 2/86* | (2006.01) |

(52) U.S. Cl.
CPC ........... *C07C 15/08* (2013.01); *B01J 29/0308* (2013.01); *B01J 29/70* (2013.01); *B01J 29/7038* (2013.01); *C07C 2/864* (2013.01); *C07C 15/04* (2013.01); *C07C 15/06* (2013.01); *C07C 2529/70* (2013.01); *Y02P 20/52* (2015.11)

(58) Field of Classification Search
CPC .............................. C07C 2/864; C07C 2/865
USPC .................................................. 585/467, 469
See application file for complete search history.

(56) References Cited

U.S. PATENT DOCUMENTS

| | | |
|---|---|---|
| 3,755,483 A | 8/1973 | Burress |
| 3,965,208 A * | 6/1976 | Butter ..................... C07C 2/865 |
| | | 585/467 |
| 4,002,698 A | 1/1977 | Kaeding |
| 4,016,218 A | 4/1977 | Haag et al. |
| 5,488,194 A | 1/1996 | Beck et al. |
| 5,545,788 A | 8/1996 | Cheng et al. |
| 5,939,597 A | 8/1999 | Dessau et al. |
| 6,423,879 B1 | 7/2002 | Brown et al. |
| 6,504,072 B1 | 1/2003 | Brown et al. |
| 6,642,426 B1 | 11/2003 | Johnson et al. |
| 7,396,967 B2 | 7/2008 | Iaccino et al. |
| 7,453,018 B2 | 11/2008 | Dakka et al. |
| 7,737,313 B2 | 6/2010 | Elia et al. |
| 7,816,574 B2 | 10/2010 | Clark |
| 8,436,222 B2 | 5/2013 | Ghosh et al. |
| 8,981,169 B2 | 3/2015 | Iaccino et al. |
| 9,095,831 B2 * | 8/2015 | Han ........................... B01J 8/34 |
| 2005/0075524 A1 | 4/2005 | Feng et al. |
| 2012/0036889 A1 * | 2/2012 | Iaccino ..................... C07C 2/76 |
| | | 62/618 |
| 2012/0083637 A1 | 4/2012 | Clem et al. |
| 2014/0128651 A1 | 5/2014 | Butler et al. |
| 2015/0175507 A1 | 6/2015 | Bender et al. |
| 2015/0376086 A1 | 12/2015 | Tinger et al. |
| 2016/0221893 A1 | 8/2016 | Ravishankar et al. |
| 2016/0264495 A1 * | 9/2016 | Molinier ................... C07C 6/06 |
| 2018/0099913 A1 | 4/2018 | Chen |
| 2018/0099915 A1 | 4/2018 | Chen |
| 2018/0170831 A1 | 6/2018 | Jan et al. |

FOREIGN PATENT DOCUMENTS

| | | |
|---|---|---|
| CN | 103263946 A | 8/2013 |
| WO | 2004/000767 A1 | 12/2003 |
| WO | 2015/094500 | 6/2015 |
| WO | 2018/067281 | 4/2018 |

OTHER PUBLICATIONS

Zhu, Z., et al., "Catalytic performance of MCM-22 zeolite for alkylation of toluene with methanol", Catalysis Today, vol. 93-95, pp. 321-325, 2004.

Yashima, T. et al.; "Alkylation on Synthetic Zeolites I. Alkylation of Toluene with Methanol", vol. 16, No. 3, (Mar. 1, 1970), pp. 273-280.

* cited by examiner

*Primary Examiner* — Thuan D Dang

(57) ABSTRACT

A process is described for producing paraxylene, in which an aromatic hydrocarbon feedstock comprising benzene and/or toluene is contacted with an alkylating reagent comprising methanol and/or dimethyl ether in an alkylation reaction zone under alkylation conditions in the presence of an alkylation catalyst to produce an alkylated aromatic product comprising xylenes. The alkylation catalyst comprises a molecular sieve having a Constraint Index≤5, and the alkylation conditions comprise a temperature less than 500° C. The alkylation catalyst may be selectivated to produce a higher than equilibrium amount of paraxylene by using a molar ratio of alkylating agent to aromatic of at least 1:4.

28 Claims, 2 Drawing Sheets

PROCESS FOR SELECTIVATING CATALYST FOR PRODUCING PARAXYLENE BY METHYLATION OF BENZENE AND/OR TOLUENE

CROSS REFERENCE TO RELATED APPLICATION

This application is a continuation of and claims benefit to U.S. patent application Ser. No. 15/702,469, filed Sep. 12, 2017, which in turn, claims benefit of U.S. Provisional Patent Application Ser. No. 62/437,493, filed Dec. 21, 2016, the contents of both of which are hereby incorporated by reference in their entireties.

FIELD

This disclosure relates to a process for selectivating a catalyst for the methylation of benzene and/or toluene to produce xylenes, particularly paraxylene.

BACKGROUND

Xylenes are valuable precursors in the chemical industry. Of the three xylene isomers, paraxylene is the most important since it is a starting material for manufacturing terephthalic acid, which is itself a valuable intermediate in the production of synthetic polyester fibers, films, and resins. Currently, the demand for paraxylene is growing at an annual rate of 5-7%.

One known route for the manufacture of paraxylene is by the methylation of benzene and/or toluene. For example, U.S. Pat. No. 6,504,072 discloses a process for the selective production of paraxylene which comprises reacting toluene with methanol under alkylation conditions in the presence of a catalyst comprising a porous crystalline material having a Diffusion Parameter for 2,2 dimethylbutane of about 0.1-15 $sec^{-1}$ when measured at a temperature of 120° C. and a 2,2 dimethylbutane pressure of 60 torr (8 kPa). The porous crystalline material is preferably a medium-pore zeolite, particularly ZSM-5, which has been severely steamed at a temperature of at least 950° C. The alkylation conditions include a temperature between about 500 and 700° C., a pressure of between about 1 atmosphere and 1000 psig (100 and 7000 kPa), a weight hourly space velocity between about 0.5 and about 1000 and a molar ratio of toluene to methanol of at least about 0.2.

In addition, U.S. Pat. No. 6,642,426 discloses a process for alkylating an aromatic hydrocarbon reactant, especially toluene, with an alkylating reagent comprising methanol to produce an alkylated aromatic product, comprising: introducing the aromatic hydrocarbon reactant into a reactor system at a first location, wherein the reactor system includes a fluidized bed reaction zone comprising a temperature of 500 to 700° C. and an operating bed density of about 300 to 600 $kg/m^3$, for producing the alkylated aromatic product; introducing a plurality of streams of said alkylating reactant directly into said fluidized bed reaction zone at positions spaced apart in the direction of flow of the aromatic hydrocarbon reactant, at least one of said streams being introduced at a second location downstream from the first location; and recovering the alkylate aromatic product, produced by reaction of the aromatic reactant and the alkylating reagent, from the reactor system. The preferred catalyst is ZSM-5 which has been selectivated by high temperature steaming.

As exemplified by the U.S. Patents discussed above, current processes for the alkylation of benzene and/or toluene with methanol are conducted at high temperatures, i.e., between 500 to 700° C. in the presence of a medium pore size zeolite, particularly ZSM-5. This results in a number of problems, particularly in that catalyst life per cycle is relatively short and so frequent regeneration of the catalyst is required. In addition, the existing processes typically result in significant quantities of methanol being converted to ethylene and other light olefins which reduces the yield of desirable products, such as xylenes, and increases recovery costs.

There is therefore a need for an improved process for the alkylation of benzene and/or toluene with methanol (or dimethyl ether), which increases the paraxylene selectivity of the catalyst and produces a higher than equilibrium amount of paraxylene.

SUMMARY

Toluene and/or benzene may be converted to xylenes via an alkylation reaction with methanol and/or dimethyl ether conducted under relatively mild conditions, namely a temperature less than 500° C., in the presence of an alkylation catalyst comprising a molecular sieve having a Constraint Index less than or equal to 5. The lower temperature alkylation reaction produces less light gas by-products and achieves longer catalyst cycle life than conventional high temperature processes. Methanol utilization (i.e., percentage of methanol converted to aromatics) is also improved as compared to conventional high temperature processes.

To increase the concentration of paraxylene in the product mixture and obtain a higher than equilibrium concentration of paraxylene, the alkylation catalyst may be selectivated. In one embodiment, the alkylation catalyst is selectivated by using an alkylating agent to aromatic molar ratio of at least 1:4 until the target paraxylene selectivity is reached. Once the target paraxylene selectivity is achieved, the molar ratio of alkylating agent to aromatic may be maintained or decreased.

DETAILED DESCRIPTION OF THE EMBODIMENTS

Figure 1:
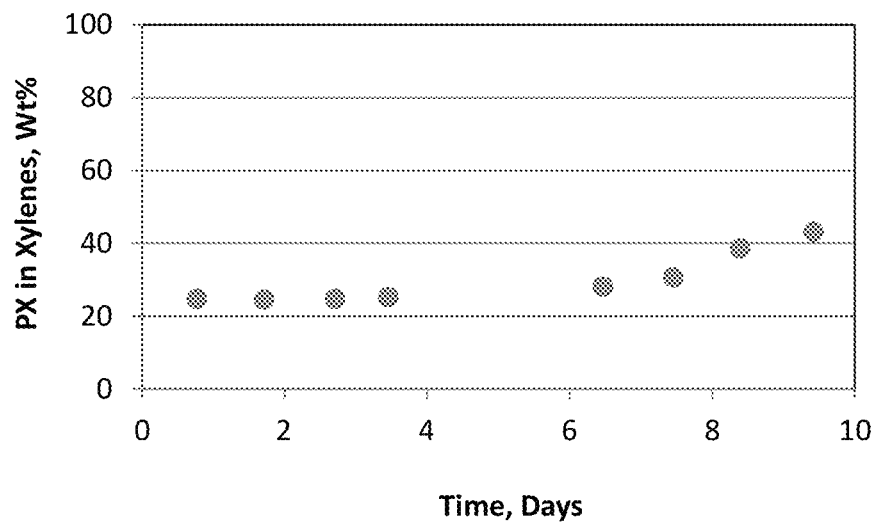
FIG. 1 is a graph of paraxylene selectivity against time on stream in the process of alkylating toluene with methanol described in the Example.

Embodiments disclosed herein provide alkylation processes for producing xylenes, particularly paraxylene, that can be conducted under relatively mild conditions to produce xylenes with less light gas by-products and longer catalyst cycle life than conventional high temperature processes. Methanol utilization (i.e., percentage of methanol converted to aromatics) is also improved. In at least some embodiments, an aromatic hydrocarbon feed comprising benzene and/or toluene is contacted with an alkylating reagent comprising methanol and/or dimethyl ether in at least one alkylation reaction zone in the presence of alkylation catalyst under alkylation conditions. The alkylation catalyst comprises a molecular sieve having a Constraint Index less than 5, such as less than 4, for example less than 3, or in some embodiments less than 2, and the alkylation conditions comprise a temperature less than 500° C.

The process is effective to convert the benzene and/or toluene to xylenes with essentially 100% methanol conversion and substantially no light gas make. The high methanol utilization is surprising in light of the methanol utilization in the prior art toluene and/or benzene methylation processes, and results in the substantial advantages of less coke formation, which increases the catalyst life. Furthermore, in prior art processes, it is preferred to co-feed steam into the reactor with the methanol to minimize the methanol side reactions, and the steam negatively impacts catalyst life. With the nearly 100% of the methanol reacting with aromatic rings to produce aromatics in the inventive process, there is no need to co-feed steam, decreasing the energy demands of the process and increasing catalyst life.

The methanol selectivity to xylenes in embodiments disclosed herein is typically on the order of 80%, with the main by-products being benzene and $C_{9+}$ aromatics. The benzene can be separated from the alkylation effluent and recycled back to the alkylation reaction zone(s), while the $C_{9+}$ aromatics can be separated for blending into the gasoline pool or transalkylated with additional benzene and/or toluene to make additional xylenes. The life of the alkylation catalyst is enhanced as compared with existing processes since methanol decomposition is much less at the lower reaction temperature. Moreover, the use of a larger pore molecular sieve minimizes diffusion limitations and allows the alkylation to be carried out at commercially viable WHSVs. Additionally, when a toluene feed (one having at least 90 wt % of toluene) is used, more alkylating agent reacts with the toluene, versus other molecules such as alkylating agent or by-products of the reaction, to produce xylenes as compared to existing processes.

The amount of paraxylene in the xylenes product can be increased up to at least 35 wt % by selectivating the alkylation catalyst. In one embodiment, the alkylation catalyst is selectivated in-situ by using at least a 1:4 alkylating agent to aromatic molar ratio in the feed. After the desired paraxylene selectivity is achieved, the alkylating agent to aromatic ratio in the feed may be maintained or decreased for the remainder of the reaction. If the alkylating agent to aromatic ratio is decreased after the catalyst has been selectivated, the alkylating agent to aromatic ratio may subsequently be raised to re-selectivate the catalyst if the paraxylene selectivity of the catalyst decreases below a predetermined threshold.

As used herein, the term "$C_n$" hydrocarbon wherein n is a positive integer, e.g., 1, 2, 3, 4, 5, etc., means a hydrocarbon having n number of carbon atom(s) per molecule. The term "$C_{n+}$" hydrocarbon wherein n is a positive integer, e.g., 1, 2, 3, 4, 5, etc., means a hydrocarbon having at least n number of carbon atom(s) per molecule. The term "$C_n$" hydrocarbon wherein n is a positive integer, e.g., 1, 2, 3, 4, 5, etc., as used herein, means a hydrocarbon having no more than n number of carbon atom(s) per molecule.

As used herein, the terms "alkylating" and "methylating", or "alkylation" and "methylation" may be used interchangeably.

Constraint Index is a convenient measure of the extent to which a molecular sieve provides control of molecules of varying sizes to its internal structure. The method by which Constraint Index is determined is described fully in U.S. Pat. No. 4,016,218, which is incorporated hereby by reference for details of the method.

Examples of suitable molecular sieves having a Constraint Index less than 5 suitable for use in the present process comprise zeolite beta, zeolite Y, Ultrastable Y (USY), Ultrahydrophobic Y (UHP-Y), Dealuminized Y (Deal Y), mordenite, ZSM-3, ZSM-4, ZSM-12, ZSM-14, ZSM-18, ZSM-20 and mixtures thereof. Zeolite ZSM-3 is described in U.S. Pat. No. 3,415,736. Zeolite ZSM-4 is described in U.S. Pat. No. 4,021,947. Zeolite ZSM-12 is described in U.S. Pat. No. 3,832,449. Zeolite ZSM-14 is described in U.S. Pat. No. 3,923,636. Zeolite ZSM-18 is described in U.S. Pat. No. 3,950,496. Zeolite ZSM-20 is described in U.S. Pat. No. 3,972,983. Zeolite Beta is described in U.S. Pat. No. 3,308,069, and Re. U.S. Pat. No. 28,341. Low sodium Ultrastable Y molecular sieve (USY) is described in U.S. Pat. Nos. 3,293,192 and 3,449,070. Ultrahydrophobic Y (UHP-Y) is described in U.S. Pat. No. 4,401,556. Dealuminized Y zeolite (Deal Y) may be prepared by the method found in U.S. Pat. No. 3,442,795. Zeolite Y and mordenite are naturally occurring materials but are also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104.

One preferred class of molecular sieve suitable for use in the present process, and having a Constraint Index less than 5, are crystalline microporous materials of the MWW framework type. As used herein, the term "crystalline microporous material of the MWW framework type" includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of MWW framework topology unit cells. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Crystalline microporous materials of the MWW framework type include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Examples of crystalline microporous materials of the MWW framework type include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), UZM-8HS (described in U.S. Pat. No. 7,713,513), UZM-37 (described in U.S. Pat. No. 7,982,084), EMM-10 (described in U.S. Pat. No. 7,842,277), EMM-12 (described in U.S. Pat. No. 8,704,025), EMM-13 (described in U.S. Pat. No. 8,704,023), MIT-1 (described by Luo et. al, in Chemical Science, 2015, Vol. 6, pp. 6320-6324) and mixtures thereof, with MCM-49 generally being preferred.

In some embodiments, the crystalline microporous material of the MWW framework type employed herein may be contaminated with other crystalline materials, such as ferrierite or quartz. These contaminants may be present in quantities ≤10% by weight, normally ≤5% by weight.

Additionally or alternatively, the molecular sieves useful herein may be characterized by a ratio of silicon to aluminum. In particular embodiments, the molecular sieves suitable herein include those having a Si/Al ratio of less than 100, preferably about 15 to 50.

The molecular sieve catalyst may be selectivated to produce a higher than equilibrium amount of paraxylene, that is more than about 23 wt % of paraxylene, based on the total amount of xylenes, in the product mixture. In one embodiment, the concentration of paraxylene in the xylene fraction is at least 35 wt %, preferably at least 40 wt %, and more preferably at least 45 wt %. The selectivation of the catalyst may be conducted in-situ by using a feed with an alkylating agent to aromatic ratio of at least 1:4, or 1:3, or 1:2 until the target paraxylene selectivity is reached. As used herein, the target paraxylene selectivity means at least 35 wt %, preferably at least 40 wt %, and more preferably at least 45 wt % of paraxylene in the xylenes fraction. Once the target paraxylene selectivity is achieved, the alkylating agent to aromatic ratio of the feed may be decreased, though in some embodiments, the alkylating agent to aromatic ratio is maintained even after the target paraxylene selectivity is achieved. If the alkylating agent to aromatic ratio is decreased once the catalyst is sufficiently selectivated, and the paraxylene selectivity decreases below the target paraxylene selectivity, the alkylating agent to aromatic ratio of the feed may again be increased to re-selectivate the catalyst.

The catalyst may additionally or alternatively be selectivated, either before introduction into the aromatization reactor or in-situ in the reactor, by contacting the catalyst with a selectivating agent, such as silicon, steam, coke, or a combination thereof. In one embodiment, the catalyst is silica-selectivated by contacting the catalyst with at least one organosilicon in a liquid carrier and subsequently calcining the silicon-containing catalyst in an oxygen-containing atmosphere, e.g., air, at a temperature of 350 to 550° C. A suitable silica-selectivation procedure is described in U.S. Pat. No. 5,476,823, the entire contents of which are incorporated herein by reference. In another embodiment, the catalyst is selectivated by contacting the catalyst with steam. Steaming of the zeolite is effected at a temperature of at least about 950° C., preferably about 950 to about 1075° C., and most preferably about 1000 to about 1050° C., for about 10 minutes to about 10 hours, preferably from 30 minutes to 5 hours. The selectivation procedure, which may be repeated multiple times, alters the diffusion characteristics of the molecular sieve and may increase the xylene yield.

In addition to, or in place of, silica or steam selectivation, the catalyst may be subjected to coke selectivation. This optional coke selectivation typically involves contacting the catalyst with a thermally decomposable organic compound at an elevated temperature in excess of the decomposition temperature of said compound but below the temperature at which the crystallinity of the molecular sieve is adversely affected. Further details regarding coke selectivation techniques are provided in the U.S. Pat. No. 4,117,026, incorporated by reference herein. In some embodiments, a combination of silica selectivation and coke selectivation may be employed.

It may be desirable to combine the molecular sieve, prior to selectivating, with at least one oxide modifier, such as at least one oxide selected from elements of Groups 2 to 4 and 13 to 16 of the Periodic Table. Most preferably, said at least one oxide modifier is selected from oxides of boron, magnesium, calcium, lanthanum, and most preferably phosphorus. In some cases, the molecular sieve may be combined with more than one oxide modifier, for example a combination of phosphorus with calcium and/or magnesium, since in this way it may be possible to reduce the steaming severity needed to achieve a target diffusivity value. In some embodiments, the total amount of oxide modifier present in the catalyst, as measured on an elemental basis, may be between about 0.05 and about 20 wt %, and preferably is between about 0.1 and about 10 wt %, based on the weight of the final catalyst. Where the modifier includes phosphorus, incorporation of modifier into the catalyst is conveniently achieved by the methods described in U.S. Pat. Nos. 4,356,338, 5,110,776, 5,231,064, and 5,348,643, the entire disclosures of which are incorporated herein by reference.

The above molecular sieves may be used as the alkylation catalyst employed herein without any binder or matrix. Alternatively, the molecular sieves may be composited with another material which is resistant to the temperatures and other conditions employed in the alkylation reaction. Such materials include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of molecular sieve and inorganic oxide matrix vary widely, with the sieve content ranging from about 1 to about 90 wt % and more usually, particularly, when the composite is prepared in the form of beads, in the range of about 2 to about 80 wt % of the composite.

The feeds to the present process comprise an aromatic hydrocarbon feed, comprising benzene and/or toluene, and an alkylating reagent comprising methanol and/or dimethyl ether. Any refinery aromatic feed can be used as the source of the benzene and/or toluene, although in some embodiments it may be desirable to use an aromatic hydrocarbon feed which comprises at least 90 wt % toluene. In addition, in some embodiments, it may be desirable to pre-treat the aromatic hydrocarbon feed to remove catalyst poisons, such as nitrogen and sulfur-compounds. In other embodiments, the feed may further include non-aromatics, such as a refinery aromatic feed from which the non-aromatics have not been extracted.

The present alkylation process is conducted at relatively low temperatures, namely less than 500° C., such as less than 475° C., or less than 450° C., or less than 425° C., or less than 400° C. In order to provide commercially viable reaction rates, the process may be conducted at temperatures of at least 250° C., such as least 275° C., for example least 300° C. In terms of ranges, the process may be conducted at temperatures ranging from 250 to less than 500° C., such as from 275 to 475° C., for example from 300 to 450° C. Operating pressures will vary with temperature but generally are at least 700 kPa-a, such as at least 1000 kPa-a, for example at least 1500 kPa-a, or at least 2000 kPa-a, up to about 7000 kPa-a, for example up to about 6000 kPa-a, up to about 5000 kPa-a. In terms of ranges, operating pressures may range from 700 kPa-a to 7000 kPa-a, for example from 1000 kPa-a to 6000 kPa-a, such as from 2000 kPa-a to 5000 kPa-a. Suitable WHSV values based on total aromatic and alkylating reagent feeds are in the range from 50 to 0.5 $hr^{-1}$, such as in the range from 10 to 1 $hr^{-1}$. In some embodiments, at least part of the aromatic feed, the methanol alkylating reagent and/or the alkylation effluent may be present in the alkylation reaction zone in the liquid phase.

The alkylation reaction can be conducted in any known reactor system including, but not limited to, a fixed bed reactor, a moving bed reactor, a fluidized bed reactor and a reactive distillation unit. In addition, the reactor may comprise a single reaction zone or multiple reaction zones located in the same or different reaction vessels. In addition, injection of the methanol/dimethyl ether alkylating agent can be effected at a single point in the reactor or at multiple points spaced along the reactor.

The product of the alkylation reaction comprises xylenes, benzene and/or toluene (both residual and coproduced in the process), $C_{9+}$ aromatic hydrocarbons, co-produced water, oxygenate by-products, and in some cases, unreacted methanol. It is, however, generally preferred to operate the process so that all the methanol is reacted with the aromatic hydrocarbon feed and the alkylation product is generally free of residual methanol. The alkylation product is also generally free of light gases generated by methanol decomposition to ethylene and other olefins. In some embodiments, the organic component of the alkylation product may contain at least 80 wt % xylenes and paraxylene may make up at least 35 wt % of the xylene fraction.

After separation of the water, the alkylation product may be fed to a separation section, such as one or more distillation columns, to recover the xylenes and separate the benzene and toluene from the $C_{9+}$ aromatic hydrocarbon by-products. The resulting benzene and toluene may be recycled to the alkylation reaction zone, while $C_{9+}$ aromatics can be recovered for blending into the gasoline pool or transalkylated with additional benzene and/or toluene to make additional xylenes. Oxygenate by-products may be removed from the alkylation product by any means known in the art, such as adsorption as described in U.S. Pat. Nos. 9,012,711, 9,434,661, and 9,205,401; caustic wash as described in U.S. Pat. No. 9,294,962; crystallization as disclosed in U.S. Pat. Nos. 8,252,967, 8,507,744, and 8,981,171; and conversion to ketones as described in U.S. Patent Publication Nos. 2016/0115094 and 2016/0115103.

The xylenes recovered from the alkylation product and any downstream $C_{9+}$ transalkylation process may be sent to a paraxylene production loop. The latter comprises paraxylene separation section, where paraxylene is conventionally separated by adsorption or crystallization, or a combination of both, and recovered. When paraxylene is separated by adsorption, the adsorbent used preferably contains a zeolite. Typical adsorbents used include crystalline alumino-silicate zeolites either natural or synthetic, such as for example zeolite X, or Y, or mixtures thereof. These zeolites are preferably exchanged by cations such as alkali or alkaline earth or rare earth cations. The adsorption column is preferably a simulated moving bed column (SMB) and a desorbent, such as for example paradiethylbenzene, paradifluorobenzene, diethylbenzene, or toluene, or mixtures thereof, is used to recover the selectively adsorbed paraxylene. Commercial SMB units that are suitable for use in the inventive process are PAREX™ or ELUXYL™.

The invention will now be more particularly described with reference to the following non-limiting Example and the accompany drawings.

Example

An experiment was conducted to investigate the paraxylene selectivity in the alkylation of toluene with methanol at a temperature of 350° C., a pressure of 600 psig (4238 kPa-a) and a WHSV of 3.5 $hr^{-1}$ based on total feed. The feed used during the selectivation procedure consisted of a mixture of methanol and toluene in the molar ratio of 1:2. The catalyst used in the study is a formulated MCM-49 extrudate (80% zeolite/20% alumina binder). The reaction was carried out in a down flow fixed bed reactor. The liquid product was collected and analyzed by a 6890 Agilent GC. The gas yield was calculated by difference. The results are summarized in FIGS. 1-3.

FIG. 1 shows the selectivation for paraxylene over the nine day test. For the first four days, paraxylene selectivity was about 25 wt %, but after 9 days on stream with the higher methanol to toluene ratio of the feed, the paraxylene selectivity increased to about 43 wt %. It is expected that the paraxylene selectivity will continue to increase with the increased methanol to toluene ratio until it reaches at least 40 wt %.

Figure 2:
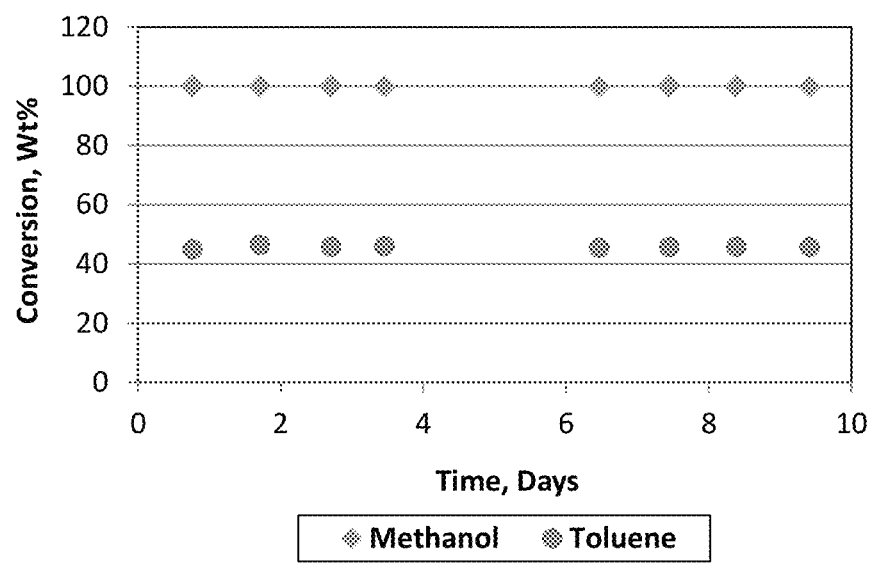
FIG. 2 is a graph of toluene and methanol conversion against time on stream in the process of alkylating toluene with methanol described in the Example.

As can be seen from FIG. 2, methanol conversion is essentially 100%. No methanol was detected in the product throughout the run. Toluene conversion is stable over the nine day test. Average toluene conversion is 45%.

Figure 3:
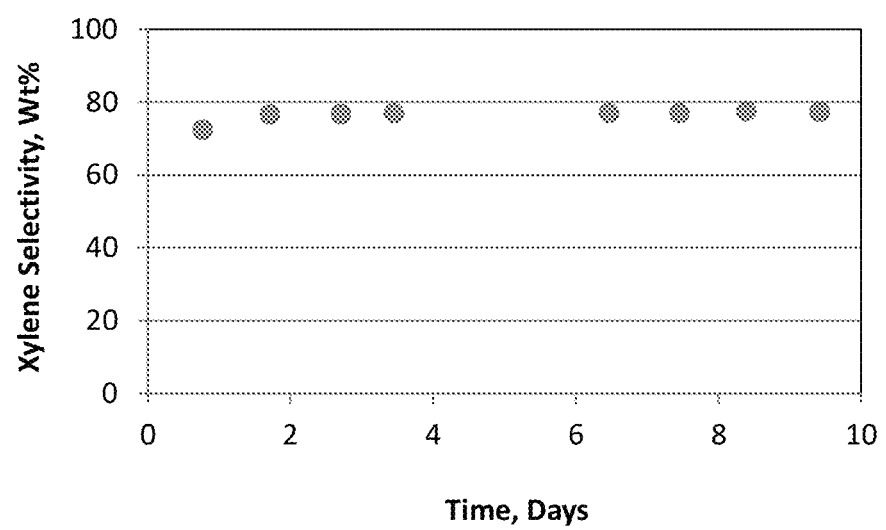
FIG. 3 is a graph of xylenes selectivity against time on stream in the process of alkylating toluene with methanol described in the Example.

Overall xylenes selectivity observed in the experiment is summarized in FIG. 3, from which it will be seen that the average xylene selectivity over the nine day test is at or near 77 wt %. The balance of the products is primarily $C_{9+}$ aromatics, with some $C_{10+}$ aromatics and benzene.

All patents, test procedures, and other documents cited herein, including priority documents, are fully incorporated by reference to the extent such disclosure is not inconsistent and for all jurisdictions in which such incorporation is permitted.

While the illustrative forms disclosed herein have been described with particularity, it will be understood that various other modifications will be apparent to and can be readily made by those skilled in the art without departing from the spirit and scope of the disclosure. Accordingly, it is not intended that the scope of the claims appended hereto be limited to the example and descriptions set forth herein, but rather that the claims be construed as encompassing all the features of patentable novelty which reside herein, including all features which would be treated as equivalents thereof by those skilled in the art to which this disclosure pertains.

When numerical lower limits and numerical upper limits are listed herein, ranges from any lower limit to any upper limit are contemplated.

The invention claimed is:

1. A process for producing paraxylene, the process comprising:
   (a) contacting an aromatic hydrocarbon feed comprising toluene with an alkylating reagent comprising methanol and/or dimethyl ether in at least one alkylation reaction zone in the presence of an alkylation catalyst and under alkylation conditions comprising a temperature less than 500° C. and a pressure of 1000 kPa-a to 7000 kPa-a to produce an alkylated aromatic product comprising xylenes,
   wherein the molar ratio of the alkylating reagent to toluene of at least 1:4 is used at least until a target paraxylene selectivity is achieved; and the alkylation catalyst comprises (i) at least one molecular sieve of the WNW framework structure; or (ii) at least one molecular sieve of the MWW framework structure and a binder; and
   (b) recovering paraxylene from the alkylated aromatic product.

2. The process of claim 1, wherein the target paraxylene selectivity comprises at least 35 wt % of paraxylene, based on the total amount of xylenes.

3. The process of claim 1, wherein the aromatic hydrocarbon feed comprises at least 90 wt % toluene.

4. The process of claim 3, wherein the alkylating reagent comprises methanol.

5. The process of claim 4, wherein the alkylation conditions comprise a temperature of at least 250° C. to less than 450° C.

6. The process of claim 5, wherein the alkylation conditions comprise a temperature from 00° C. to 400° C.

7. The process of claim 6, wherein the alkylation conditions comprise a weight hourly space velocity based on the aromatic hydrocarbon feed of 50 to 0.5 $hr^{-1}$.

8. The process of claim 7, wherein the alkylated aromatic product comprises at least 70 wt % xylenes.

9. The process of claim 1, wherein the alkylation catalyst comprises at least one molecular sieve selected from the group consisting of MCM-22, PSH-3, SSZ-25, ERB-1, ITQ-1, ITQ-2, MCM-36, MCM-49, MCM-56, EMM-10, EMM-12, EMM-13, UZM-8, UZM-8HS, UZM-37, MIT-1, and mixtures thereof.

10. The process of claim 9, wherein the alkylation catalyst comprises MCM-49.

11. The process of claim 1, wherein the alkylation catalyst consists of at least one molecular sieve of the MWW framework structure and a binder.

12. The process of claim 11, wherein the hinder is an inorganic oxide matrix.

13. The process of claim 1, wherein:
   the aromatic hydrocarbon feed comprises at least 90 wt % toluene,
   the alkylating reagent comprises methanol,
   the alkylation conditions comprise a temperature of at least 250° C. to less than 400° C., a pressure of at least 1500 kPa-a, and a weight hourly space velocity based on the aromatic hydrocarbon teed of 10 $hr^{-1}$ to 1 $hr^{-1}$,
   the at least one molecular sieve is MCM-49, MCM-22, or a mixture thereof, and
   contacting the aromatic hydrocarbon feed with the alkylating reagent in the at least one alkylation zone yields an average xylene selectivity of at least 77 wt %.

14. The process of claim 1, wherein:
   the aromatic hydrocarbon feed comprises at least 90 wt % toluene,
   the alkylating reagent comprises methanol,
   the alkylation conditions comprise a temperature of at least 250° C. to less than 400° C., a pressure of at least 1500 kPa-a; and a weight hourly space velocity based on the aromatic hydrocarbon feed of 10 $hr^{-1}$ to 1 $hr^{-1}$,
   the at least one molecular sieve is MCM-49,
   contacting the aromatic hydrocarbon feed with the alkylating reagent in the at least one alkylation zone yields an average xylene selectivity of at least 77 wt %, and
   the alkylated aromatic product is free of methanol.

15. The process of claim 1, wherein:
   the aromatic hydrocarbon feed comprises at least 90 wt % toluene,
   the alkylating reagent comprises methanol,
   the alkylation conditions comprise a temperature of at least 250° C. to less than 400° C., a pressure of at least 2000 kPa-a, and a weight hourly space velocity based on the aromatic hydrocarbon feed of 10 $hr^{-1}$ to 1 $hr^{-1}$,
   the at least one molecular sieve is MCM-49, MCM-22, or a mixture thereof,
   the aromatic hydrocarbon feed and the alkylating reagent are contacted with one another in the absence of any added steam, and
   the at least one alkylation zone comprises a fixed bed reactor.

16. The process of claim 1, wherein:
   the aromatic hydrocarbon feed comprises at least 90 wt % toluene,
   the alkylating reagent comprises methanol,
   the alkylation conditions comprise a temperature of at least 250° C. to less than 400° C., a pressure of at least 2000 kPa-a, and a weight hourly space velocity based on the aromatic hydrocarbon feed of 10 $hr^{-1}$ to 1 $hr^{-1}$,
   the at least one molecular sieve is MCM-49,
   the aromatic hydrocarbon feed and the alkylating reagent are contacted with one another in the absence of any added steam, and
   the at least one alkylation zone comprises a fixed bed reactor.

17. The process of claim 1, wherein:
   the aromatic hydrocarbon feed comprises at least 90 wt % toluene,
   the alkylating reagent comprises methanol,
   the alkylation conditions comprise a temperature of at least 250° C. to less than 400° C., a pressure of at least 4238 kPa-a, and a weight hourly space velocity based on the aromatic hydrocarbon feed of 10 $hr^{-1}$ to 1 $hr^{-1}$,
   the at least one molecular sieve is MCM-49, MCM-22, or a mixture thereof, and
   contacting the aromatic hydrocarbon feed with the alkylating reagent in the at least one alkylation zone yields an average xylene selectivity of at least 77 wt %.

18. The process of claim 1, further comprising decreasing the molar ratio of the alkylating reagent to toluene after the target paraxylene selectivity is achieved.

19. The process of claim 18, wherein, after decreasing the molar ratio of the alkylating reagent to toluene, the paraxylene selectivity decreases below a predetermined threshold, the process further comprising increasing the molar ratio of the alkylating reagent to toluene to increase the paraxylene selectivity.

20. A process for selectivating an alkylation catalyst for the alkylation of toluene, the process comprising:
(a) providing an alkylation catalyst in at least one alkylation reaction zone, wherein the alkylation catalyst consists of (i) at least one molecular sieve of the MWW framework structure; or (ii) at least one molecular sieve of the MWW framework structure and a binder;
(contacting the alkylation catalyst with an aromatic hydrocarbon feed comprising toluene with an alkylating reagent comprising methanol under alkylation conditions comprising a temperature from about 250° C. to less than 500° C. and a pressure of 1000 kPa-a to 7000 kPa-a to produce an alkylated aromatic product comprising xylenes;
wherein at least a 1:4 molar ratio of alkylating reagent to toluene in the aromatic hydrocarbon feed is used until a target paraxylene selectivity is achieved; and
(c) recovering paraxylene from the alkylated aromatic product.

21. The process of claim 20, wherein the target paraxylene selectivity comprises at least 35 wt % of paraxylene, based on the total amount of xylenes.

22. The process of claim 20, wherein the aromatic hydrocarbon feed comprises at least 90 wt % toluene.

23. The process of claim 22, wherein the alkylation conditions comprise a temperature from 300° C. to less than 450° C.

24. The process of claim 23, wherein the alkylation conditions comprise a weight hourly space velocity based on the aromatic hydrocarbon feed of 50 to 0.5 $hr^{-1}$.

25. The process of claim 24, wherein the alkylated aromatic product comprises at least 70 wt % xylenes.

26. The process of claim 25, wherein the alkylation catalyst comprises at least one molecular sieve selected from the group consisting of MCM-22, PSH-3, SSZ-25, ERB-1, ITQ-1, ITQ-2, MCM-36, MCM-49, MCM-56, EMM-10, EMM-12, EMM-13, UZM-8, UZM-8HS, UZM-37, MIT-1, and mixtures thereof.

27. The process of claim 26, wherein the alkylation catalyst comprises MCM-49.

28. The process of claim 20, wherein the alkylation catalyst consists of at least one molecular sieve of the MWW framework structure and a binder, and wherein the binder is an inorganic oxide matrix.

* * * * *